(12) United States Patent
Sarkis, Jr. et al.

(10) Patent No.: US 9,390,458 B2
(45) Date of Patent: Jul. 12, 2016

(54) NETWORK FOR HEALTH MANAGEMENT AND MOBILE DEVICE CONTROLLED ACCESS

(71) Applicant: Pharma-Smart International, Inc., Rochester, NY (US)

(72) Inventors: Frederick W. Sarkis, Jr., Rochester, NY (US); Joseph O. Sarkis, Vancouver (CA); Lisa Goodwin, Penfield, NY (US)

(73) Assignee: PHARMA-SMART INTERNATIONAL, INC., Rochester, NY (US)

( * ) Notice: Subject to any disclaimer, the term of this patent is extended or adjusted under 35 U.S.C. 154(b) by 0 days.

(21) Appl. No.: 14/029,081

(22) Filed: Sep. 17, 2013

(65) Prior Publication Data

US 2014/0014720 A1    Jan. 16, 2014

Related U.S. Application Data

(63) Continuation-in-part of application No. 12/994,218, filed as application No. PCT/US2009/045141 on May 26, 2009, now Pat. No. 8,534,549, and a continuation-in-part of application No. 12/196,021, (Continued)

(51) Int. Cl.
*G06F 17/00* (2006.01)
*G06K 5/00* (2006.01)

(Continued)

(52) U.S. Cl.
CPC .............. *G06Q 50/22* (2013.01); *G06F 19/322* (2013.01); *G06F 19/3418* (2013.01); *G06Q 50/24* (2013.01)

(58) Field of Classification Search
CPC .... A61B 5/0002; A61B 5/0004; G06Q 50/22; G06Q 50/24; G07F 17/00; G06F 19/322; G06F 19/3418

USPC ......... 235/375, 380, 382, 435, 487; 705/2–3; 600/300

See application file for complete search history.

(56) References Cited

U.S. PATENT DOCUMENTS

| 5,307,263 A | 4/1994 | Brown |
| 5,793,027 A | 8/1998 | Baik |

(Continued)

FOREIGN PATENT DOCUMENTS

| FR | 2680258 A1 | 2/1993 |
| KR | 1020050018323 A | 2/2005 |

(Continued)

OTHER PUBLICATIONS

ISA/KR, International Search Report of prior International Appl. No. PCT/US2009/045141 dated Jan. 1, 2010, total 4 pages.

(Continued)

*Primary Examiner* — Laura Gudorf
(74) *Attorney, Agent, or Firm* — Christopher E. Blank, Esq.; Schmeiser, Olsen & Watts, LLP

(57) ABSTRACT

A system comprises a database configured to be coupled to a public wide area network. One or more non-invasive physiological test machines are also configured to be coupled to the public wide area network and are registered at the database for performing one or more non-invasive physiological tests for authorized users. A plurality of electronic readers and/or scanners are each associated with at least one of the physiological test machines for controlling use thereof and for reading machine readable codes presented to the electronic reader/scanner. The machine readable code has associated therewith a number of remaining authorized uses, an authorized time period, and an identification code associated with an authorized user. Records of the non-invasive physiological test results are stored in the database according to the identification code, wherein the machine readable code, the identification code, and the data representative of the non-invasive physiological test results do not carry information representative of the identity of the authorized user.

20 Claims, 9 Drawing Sheets

Related U.S. Application Data filed on Aug. 21, 2008, now Pat. No. 8,061,594, which is a continuation-in-part of application No. 11/502,738, filed on Aug. 11, 2006, now Pat. No. 7,438,223.

(60) Provisional application No. 60/708,125, filed on Aug. 12, 2005.

(51) Int. Cl.
  *G06K 7/00* (2006.01)
  *G06K 15/00* (2006.01)
  *G06K 19/00* (2006.01)
  *G06Q 10/00* (2012.01)
  *G06Q 50/22* (2012.01)
  *G06F 19/00* (2011.01)
  *G06Q 50/24* (2012.01)

(56) References Cited

U.S. PATENT DOCUMENTS

| | | | |
|---|---|---|---|
| 5,827,179 A | 10/1998 | Lichter et al. | |
| 6,283,369 B1 | 9/2001 | Kurokawa et al. | |
| 6,378,073 B1 | 4/2002 | Davis et al. | |
| 6,524,240 B1 | 2/2003 | Thede | |
| 6,563,596 B1 | 5/2003 | Narushima | |
| 6,712,762 B1 | 3/2004 | Lichter et al. | |
| 7,438,223 B2 | 10/2008 | Sarkis et al. | |
| 8,061,594 B2 | 11/2011 | Sarkis et al. | |
| 2001/0025226 A1* | 9/2001 | Lavery | 702/108 |
| 2003/0130567 A1* | 7/2003 | Mault et al. | 600/300 |
| 2004/0117309 A1 | 6/2004 | Inoue et al. | |
| 2004/0167381 A1 | 8/2004 | Lichter et al. | |
| 2005/0075543 A1* | 4/2005 | Calabrese | 600/300 |
| 2006/0020517 A1 | 1/2006 | Brooks et al. | |
| 2006/0259328 A1* | 11/2006 | Burd et al. | 705/2 |
| 2007/0057041 A1 | 3/2007 | Sarkis et al. | |
| 2007/0231846 A1 | 10/2007 | Cosentino et al. | |
| 2008/0046366 A1* | 2/2008 | Bemmel et al. | 705/44 |
| 2009/0212917 A1* | 8/2009 | Chang et al. | 340/10.1 |

FOREIGN PATENT DOCUMENTS

| | | |
|---|---|---|
| KR | 1020070102639 A | 10/2007 |
| WO | WO 99-44162 | 9/1999 |
| WO | WO 03-073353 | 9/2003 |
| WO | WO 2007-022017 A2 | 2/2007 |

OTHER PUBLICATIONS

Australian Government, IP Australia, Examination Report of corresponding AU Appl. No. 2009248794 dated Feb. 28, 2014 (3 pgs.).
WIPO, International Search Report dated Mar. 28, 2007 in International Application PCT/US2006/031519.

* cited by examiner

NETWORK FOR HEALTH MANAGEMENT AND MOBILE DEVICE CONTROLLED ACCESS

CROSS-REFERENCE TO RELATED APPLICATIONS

This application is a continuation-in-part of U.S. patent application Ser. No. 12/994,218 filed Nov. 23, 2010, now U.S. Pat. No. 8,534,549, issued on an even date herewith Sep. 17, 2013, which is a U.S. national stage Rule 371 filing of International Application No. PCT/US2009/045141, filed on May 26, 2009; which is a continuation-in-part of U.S. patent application Ser. No. 12/196,021 filed Aug. 21, 2008, now U.S. Pat. No. 8,061,594 issued Nov. 22, 2011, which is a continuation-in-part of U.S. patent application Ser. No. 11/502,738 filed Aug. 11, 2006, now U.S. Pat. No. 7,438,223, issued on Oct. 21, 2008, which claims priority to U.S. Provisional Application No. 60/708,125 filed Aug. 12, 2005. The patents and patent applications identified above are incorporated by reference herein in their entireties.

BACKGROUND

The present invention relates to a network that uses machine readable cards or hand held communication devices, including and not limited to smart cards or smart phones, for authorizing access to one or more controlled resources such as blood pressure test machines, and for the management of biometric data, including and not limited to blood pressure, stored on the smart cards or hand held communication devices, and on a secure network.

SUMMARY

The embodiments of the invention described herein show, in their broader aspects, systems and methods for authorizing access to controlled resources. One particular resource is a non-invasive physiological test machine, such as a blood pressure measurement machine. Other controlled resources are access to passage on a transit system, renting, leasing or borrowing articles such as vehicles, machines, equipment, DVDs, video tapes and books, or renting a hotel room or a house.

One embodiment is a system that uses machine readable cards, hand held communication devices, such as smart cards (cards with electronic circuits thereon) or smart phones, card readers, scanners, such as laser scanners for reading one and two-dimensional bar codes, biometric scanners, such as finger print scanners, retinal scanners, and facial recognition software, and user interface displays, for controlling access to one or more controlled resources via a public wide area network and a remote database. Although the discussion that follows makes consistent reference to a user identification device, it will be understood that, in addition to smart cards and smart phones, such user identification devices may include a card having a one or two dimensional bar code imprinted thereon such as a QR code. The machine readable cards or hand held communication devices carry a unique code and data that represent one or more or an unlimited number of authorized uses of the controlled resource over a limited or unlimited period of time of use. Card readers, scanners, e.g. bar code or biometric scanners, or a combination thereof are found at locations of the controlled resource. The card or hand held communication device must be swiped, inserted, presented, or displayed, into or at the card reader or scanner at the controlled resource location by the user, to gain access to the controlled resource. The card readers or scanners detect a unique code on the card or hand held communication device to verify that the presenter is an authorized user. The card readers or scanners may also electronically access a remote database over a network to determine the remaining number of authorized uses and the time of authorized use of the controlled resource. If the requested access is within the authorized period of use and the card or hand held communication device indicates at least one authorized use remaining, the user is permitted access to the controlled resource. For example, if the controlled resource is a blood pressure machine, the user is allowed to operate the machine to take and record his or her blood pressure. If the controlled resource is an automobile, the user is allowed access to the automobile (e.g. the car door opens) and to operate the automobile. However, if there are no indicated authorized uses remaining or the authorized period of use is expired, the user may be denied access. Alternatively, use of a blood pressure machine, for example, may be permitted, if there are no authorized uses remaining, and the measurement results generated thereby may be provided to the user, but are not transmitted to a centralized remote database for overall tracking and health management purposes as is described herein.

The location of the controlled resource or the controlled resource itself has a display. The display is coupled to a card reader or scanner and is responsive to a recognition of an authorized user for showing the number of remaining authorized uses of the controlled resource and the expiration date of the authorized period of use. At each location or on each controlled resource there is a transmitter that is coupled to the controlled resource, to a wide area public access network, such as a public telephone network, a private computer network, the internet, or any combination thereof. The transmitter may be coupled to a public network over a modem, such as a cable modem, or may be coupled via a 3G/4G cellular network transceiver or over other wireless transceiver components such as WiFi compatible modules. The network is also connected to a remote database accessible by the controlled resource. The transmitter sends data representative of the location of the card reader or scanner, the use of the controlled resource and the time of use of the controlled resource via the network to the remote database, through a network service interface. As used in this patent, the term "network service interface" includes and is not limited to one or more computers, such as servers or work stations. Each network interface service facilitates communication between a private network operated by a receiver company and one or more sending entities which send data or inquiries to the receiver company. The data bases operated by the receiver company may be a single database with multiple fields or databases segmented by country, customer or another field. A further database may hold administrative data and statistics about the system and the data in the databases. Data and/or inquiries are transmitted to the receiver company from a variety of sources, including and not limited to the access controlled resource, the general public who may have limited access to data, information companies that mine data in the databases, and Partners of the receiver company who assist in providing the access controlled resource. The receiver company has data bases that hold information received from a number of transmitters including, and not limited to, data generated by the transmitters such as local, restricted resources, and the general public, health information entities, and enterprises operated by or affiliated with the company that operates the databases. One or more of the network interface services may be specially adapted or configured to communicate with one but not all of the transmitters. For example, one network interface service may be adapted to communicate with the access limited resource, while another network interface service communicates with the general public via the Wide World Web. Still other network interface services may be particularly adapted to communicate with data mining companies and still other services communicate with Partners. Each of the network interface services receives transmissions and queries from one or more of the transmitters via a private or public wide area network and records data corresponding to the use of the controlled resource in accordance with the unique code of each card or hand held communication device. The transmitter may also send results of use of the controlled resource, such as blood pressure readings, for storage in a file associated with the unique code corresponding to the card or hand held communication device.

Other embodiments of the invention provide systems, machines and methods that use the card or hand held communication device, the network, the controlled resources and a world wide web based application that provides a user interface to the databases to interconnect patients, their doctors, pharmacists, hospitals and other medical service personnel. Each smart card and hand held communication device identifier stores a unique code in the form of numeric or alpha-numeric characters, which may be printed on the card in human readable form, machine readable form, such as a one or two dimensional barcode, or a combination thereof. With respect to the hand held communication device embodiment, the unique code may be called up from a digital memory of the device and displayed on a display screen to be scanned and identified by a scanner at the location of the controlled resource. The user's name is not imprinted on the card or on the hand held communication device or provided with any data communicated or exchanged with the controlled resource or with the databases described herein. Instead, the user verifies his or her identity by logging into a database using the unique code contained on the card or in the hand held communication device. The user may then be prompted to verify the unique code by entering, reading or scanning it a second time. The user may be asked to answer one or more security questions and/or establish a personal identification number (PIN). The login does not request the name or other information that could be used to identify the individual user. The security information and/or PIN, if required, are associated with the unique code appearing on the card or hand held communication device and with a file, e.g. a user account, in the database that corresponds to the code. When the user inserts a card or presents a hand held communication device to the controlled resource, e.g. a machine or kiosk, if the user is a valid member, as verified by the unique code, and has authorized uses in an authorized time period, the machine operation is enabled. The machine, for example, may be a blood pressure machine such as the PharmaSmart Model PS-2000C, takes a blood pressure reading and uploads the reading data to the remote database and into the file which bears the unique code of the smart card or hand held communication device. If the kiosk is off line or otherwise unconnected to the database, the smart card or hand held communication device may store the readings until the next time the user takes a reading at a kiosk that is online. At that time, the stored data on the smart card or the hand held communication device is uploaded and stored in the coded file on the database.

As part of the card manufacturing process, a unique alphanumeric base 23 code may be programmed into the memory of the smart card and a matching code may be printed on the card itself. Alternatively, a hand held communication device may download and store the unique alphanumeric code via a software application ("app") download. Once downloaded, accompanying software may be activated by the user so that the unique alphanumeric code is accessed and displayed on a display screen of the hand held communication device. The display may be in the form of a one or two dimensional machine readable code, a human readable code, or a combination thereof. This unique code may be, for example, nine digits long: "AAP-XXX-ZZZ" for purposes of the discussion that follows. The blood pressure kiosk that reads and verifies the smart card or hand held communication device is connected to a database. The World Wide Web application, network service interface and database may each be at any location. In one embodiment, the network service interface and database is located on one or more networked computers that is connected to the World Wide Web or other public or private network. The kiosk communicates through the network service interface to transmit readings and related metadata associated with the unique access code on the card or hand held communication device. The network interface service then processes this data and updates the related database data associated with the unique access code with any new reads just performed or found on the smart card or hand held communication device. Each of these readings will be stored in a secure database, and will be identified by the card's or hand held communication device's unique alphanumeric code associated with the user. Information associating the unique alphanumeric code with the user will be available only at sites where the identification of the user and his or her medical information is permitted.

This system and method allow the user, or the user's healthcare provider, to access the blood pressure data via the internet using a specially designed graphic user interface (web-site) that allows the data to be presented, viewed, filtered and printed in informative and educational ways. In one embodiment, in order to view the data using an electronic network access point, the unique code associated with the user is entered into a "login" page on a website that is connected to the database. Additional information may also be required such as birth date information, for example. The user may permit others, such as physicians, pharmacists, nurses, and other healthcare providers to see the user's data by giving them the unique access code, a PIN, and other security information that may be required. Since there are no names associated with the unique ID's, the process is fully HIPAA compliant.

This system is efficient and secure. It allows the database operator to identify who issued the card or the software application ("software app") in the hand held communication device because the first three characters of the unique code identify the entity. For example, a card or hand held communication device storing or bearing the code AAP-XXX-ZZZ, for example, where the first three characters identify the organization that issued the card or information stored in the hand held communication device, or other membership identification information. For example, the characters "AAP" may stand for the "All American Pharmacy", which is a hypothetical chain of pharmacies distributed throughout the U.S.A. However, other, non-commercial organizations, such as the National Institutes of Health, could issue cards or membership identification information, such as in a software app executable in a hand held communication device, to participants in blood pressure studies and use the results of the uploaded readings to conduct one or more blind studies. Other organizations include independent pharmacies, hospitals, nursing homes, etc. This allows the distributor of the cards or of the software app stored in the hand held communication device to provide custom branding on their web-site interface. When a particular user types his or her unique code into the "log-in" website, the website is an AAP-branded "personal health record" site. This system also enables exclusivity by the card or software app issuer. For example, the blood pressure machines can be configured to accept only cards or hand held communication devices storing unique codes bearing the first three characters "AAP". Therefore, smart hand held communication devices or hand held communication devices having stored identifiers issued by another retailer or organization could be programmed to be unusable in the blood pressure machines located in All American Pharmacies.

The smart card and the hand held communication device and its database system have many applications for a variety of issuers. Its connectivity via the Web will be extremely useful for clinical trials that require the aggregate data analysis of the blood pressure of large groups of people over long periods of time. Alternatively, an employer could issue smart cards or software app for hand held communication devices to its employees to acquire data on how the employer's wellness program is working.

The system and its database may be used in conjunction with other existing or expected medical records systems, such as Electronic Medical Record (EMR) software companies (physician patient care software), MTM (Medication Therapy Management software used by pharmacies), Diabetes Diagnostic Companies (Roche, Bayer, and Lifescan), and web based Personal Health Record companies such as Microsoft HealthVault and Google's new personal health record program. Data collected from the smart cards or hand held communication devices may also be mined by geographic location.

The system can also be linked for access by various hand held personal communication devices, such as Apple's iPhone, RIM's Blackberry, Google's Android, Palm's Pre, Microsoft's Windows Mobile or other cellular phones, tablets, or laptops via custom software apps that enable secure access to specific end user data similar to the PC based web user interface application described herein.

The method, apparatus and system of the disclosed embodiments rely upon automated blood pressure ("ABP") machines and other types of non-invasive medical self-monitoring equipment, e.g., weight scales, automated glucose monitors, cholesterol monitors, blood oxygen monitors, and devices that calculate and record body-mass-index (BMI) (height information required to be provided). These machines are either purchased or leased by pharmacies, corporate work sites, health clubs and other customers. For the purpose of this discussion, these customers will be referred to as "Locations".

The Locations provide ABP and other medical self-monitoring machines as a service to their customers, employees, members, etc. For the purpose of this discussion, we will refer to these customers, employees, and members using the ABP or other medical self-monitoring machines as "user" or "end user". Such Locations often offer the end user the option to use a smart card or a hand held communication device software app to record and track their blood pressure history over time.

As used herein below, the term "user identification device" includes any memory card, smart card (i.e. card containing electronics), printed card, or electronic digital communication device that is generally of a size that can be easily carried and having power, ground, input and output ports or terminals and an array of memory cells arranged in rows and columns. The term "user identification device" also includes a smart phone, PDA, tablet, laptop or other hand held electronic communication device having an installed software module or app that may be executed to perform functions that provide it with functionality similar to that of the smart card embodiments described herein. Such devices may include additional components for implementing other functions such as digital image capture using a camera function, cellular phone communication via cellular communication towers for cell subscribers, and other functions. Such other functions may be primary functions of the user identification device or they may be ancillary functions. The memory cells are typically made of flash memory which is static memory that retains its information when electrical power is removed therefrom. Such devices include memory arrays of flash memory cells and have a microprocessor or other control or logic circuitry, as described below. One purpose of the microprocessor or other circuitry is to provide security for the data on the user identification device. Such user identification devices may have encryption and decryption keys or stored programs that secure the user identification devices from unwanted access.

Each time the end user uses the user identification device to access the controlled resource, such as a blood pressure measurement machine, the blood pressure reading, pulse rate, and the date of the measurement may be recorded on the user identification device via communication over a network or by direct storage on the identification device if the device is a smart card inserted in the controlled resource. The data collected by the ABP machines may be cumulatively stored in remote databases and may be transmitted at any time to a user's hand held communication device over wired or wireless network connections and be recorded therein. If the user identification device embodiment comprises a smart card that is inserted into the ABP machine, the machine may write the readings onto a memory of the card. Alternatively, if the user identification device embodiment comprises a smart phone, the ABP machine may also be connected to the smartphone via a wired connection, such as a USB connection, and write the readings data into a memory of the smartphone instead of over a network as described above. The ABP machine may then print out a history of the end user's most recent results (as many as 10 results), and provides a calculated average blood pressure and pulse rate for the end user. Similar monitoring, data collection, data compilation, and data presentation opportunities exist for other forms of medical self-monitoring equipment. A printed history of the end user's most recent results for any such monitoring process is important as it provides the end user with information to share with physicians, pharmacists, and other health care professionals. Recorded ABP information assists the health care professional in evaluating the end user's blood pressure history and the effectiveness of any end user hypertension control program. Recorded weight, BMI, glucose levels, cholesterol levels, blood oxygen levels, and other records of medical monitoring for the end user can likewise assist health care professionals in their care of that end user.

The embodiments enable the providers of automated blood pressure readings and other non-invasive physiological test data, such as pharmacies, corporate work sites, health clubs and other customers, to charge an annual fee for the use of an user identification device to record the non-invasive physiological test data and make the data available for health consultations.

A kiosk, machine or other controlled resource may have an operating program. That program may comprise software that is installed, for example, in a computer of an automated blood pressure machine or other medical self-monitoring system. The software may be accessed with one or more user identification devices, use a custom-formatted unique code associated with the user for keeping track of the user's non-invasive physiological test data and the dates those readings were taken. The software also provides the option to control uses of the user identification device by requiring that the user identification device be reauthorized for further uses beyond the initial authorized number of uses.

The embodiments of the invention may be applied to other, non-medical systems for recording readings and verifying usability.

DETAILED DESCRIPTION OF THE EMBODIMENTS

Figure 1:
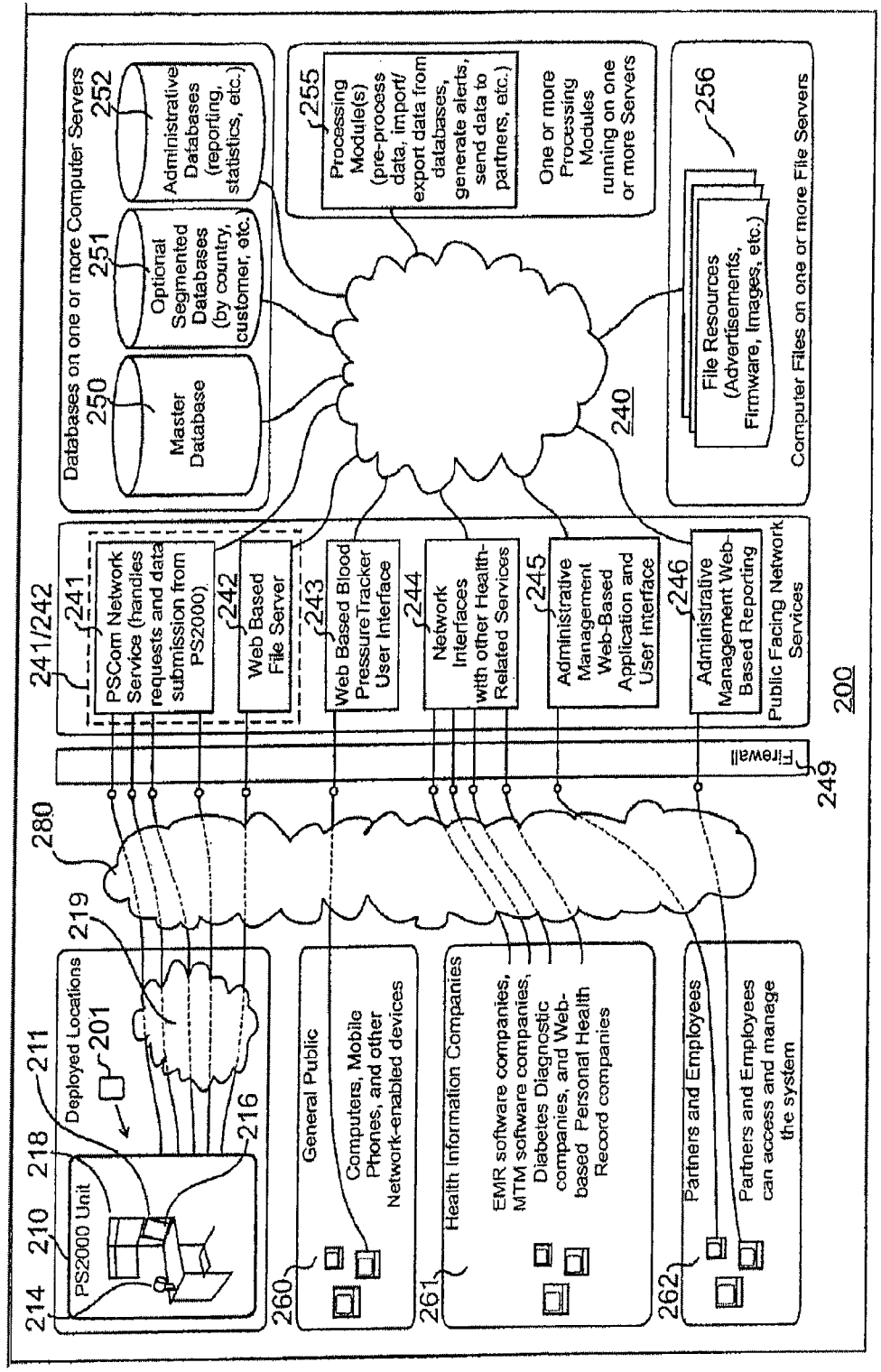
FIG. 1 is a schematic view of network using an exemplary secure user identification device.

Turning to FIG. 1, there is shown a schematic of a system 200. Kiosks or machines 210 (those terms are interchangeably herein), i.e., ABP machines, are installed at one or more deployed locations that are controlled by a Partner. As used herein, a Partner is an entity or enterprise that engages with the PharmaSmart (or a similar manufacturer or database operator) to generate valid user identification devices, such as the cards or software apps described herein, membership identification information, and permit user identification device users access to the kiosks. Such kiosks are found at pharmacy or any business or enterprise open to the public. The kiosk 210 may be a controlled resource for recording physiological data, in particular blood pressure readings, glucose readings, etc. The kiosk 210 may have a card reader, scanner, keypad or similar device for reading machine readable code, biometric data, or user input data presented to the kiosk 211 for accepting data recorded on the user identification device. A card reader may also store data in a smart card, or the kiosk may transmit and store data in a database account associated with the user in the data collection private network 240 as described below, and such data may be allowed to be transmitted to the user's identification device if it contains network communication capability. Local display 218 may be used to show current and/or recent readings of the user. One or more control buttons 216 are used to actuate the blood pressure cuff 214. Arrows 215 indicated the cuff inflating and deflating. The user identification device 201 may be used to initiate operation of the machine 210.

The machine 210 has a transmitter, modem or other device that is connected to a Partner private network 219. The Partner private network may include one or more kiosks operated by a Partner who has machines at one or more locations. The Partner private network 219 is coupled to a wide area public network 280, such as the Internet. A data collection private network 240 is also connected to the public network 280 via a firewall 249 which has an integrated collection of security measures designed to prevent unauthorized electronic access to the data collection private network 240. The machine 210 may gain access to the data collection private network 240 through the security checks made by the firewall 249 and then through one of two network interface services (NIS) 241, 242. In general, NIS 241 handles requests and data submissions, e.g., blood pressure readings, from machines 210 to the data collection private network 240 according to a unique code associated with a particular user. NIS 242 is a web-based server that parses data for Partner reports. Upon completion of a noninvasive blood pressure (NIBP) test, data from the reading and/or other data stored on the user identification device 201 and accessed by the machine 210 may be uploaded to the networks 219, 280, 240 for transmission to and storage in a master database 250. Any data uploads performed may be stored in user accounts at the data collection private network 240 and/or the master database 250 associated with the unique code provided each user as described herein. Additional health information may be obtained from a user operating the kiosk via a question and answer session presented in a user interface displayed on a display screen at the kiosk. Such information is added to the health information record at the data collection private network 240 and/or the master database 250 associated with the user's unique access code. If the user carries a portable blood glucose meter, the kiosk provides a port wherein the glucose meter may be connected to the kiosk and the glucose readings stored therein are downloaded and recorded as part of the user's health record. If the glucose meter includes a wireless communication capability, e.g., cellular, Bluetooth, NFC, the kiosk may allow the glucose readings stored therein to be downloaded wirelessly and recorded as part of the user's health record.

In one embodiment, a kiosk may be provided at a health care provider's office, such as a clinic, a pharmacy, a doctor's office, a hospital, an ambulatory care center, or other healthcare provider site. The on-site kiosk may be integrated into a health care data management utility operated by the health care provider. Access to data stored in association with a user's (patient) unique access code at the data collection private network 240 and/or the master database 250 associated with the unique code is available to the health care provider as part of the integration. The kiosk may be connected to a private or public network, such as the internet, via a wired or wireless access point, e.g. a cable provider or a cellular network provider, for exchanging information between the health care provider and the data collection private network 240. As in the normal course, biometric measurements undertaken by the kiosk are transmitted to the data collection private network 240 and/or the master database 250 associated with the user's unique code and are accessible by the health care provider and/or any software diagnostic tools that may be employed thereby.

One exemplary procedure that may be established for the health care provider's use of the on-site kiosk is to require that the provider request a unique session identifier from the data collection private network 240 for each user (patient) who will use the kiosk for one or more biometric measurements. Such a session identifier may be requested in a network communication transaction with the data collection private network 240. Such transactions, inclusive of fees, if any, may be covered by an agreement governing the health provider's use of the kiosk, related biometric data generated thereby, and network management functions. The session ID will be linked by the health care provider with the unique access code associated with the user so that data obtained during the session may be used to update the user's health records stored at the data collection private network 240. An authorization for a session ID in response to such a request may be accompanied by a response containing a session ID in the form of an alphanumerical code to be manually entered at the kiosk, or a machine readable one or two dimensional bar code transmitted to the kiosk or to the health care provider for output on a printer. The session ID may also be transmitted to the user's hand held communication device and displayed on its display screen. The user may then present or enter the authorized session identifier at the kiosk, which will validate the session ID, by reading or scanning the session ID as provided, to initiate an ABP reading or other automated clinical screening session, as described herein. The results are then transmitted to the data collection private network 240 and/or the master database 250 associated with the user's unique code and are made available to the health care provider. If the health care provider site is a part of a larger overall health care provider organization, the biometric information collected for the user (patient) may be made available throughout the organization to assist in managing the user's healthcare.

The user identification device 201 controls access to the machine 210 and/or controls access to a remote database 250 through the network interface services 241 or 242. The machine 210 is configurable to not read blood pressure unless the user identification device 210 is an authorized user identification device which may be verified by the device having been inserted, presented to or otherwise linked with the machine 210 and read or scanned, and validated. Alternatively, if the machine 210 includes biometric scanners, then the user may be validated via finger print authorization, retinal imagery, or facial recognition software. In that case, after the user is identified and validated, or the user identification device is validated, the user initiates operation of the machine 210 by pressing a control button 216. The results of the test are shown in the display or printed. The results may also be stored on the user identification device 201, transmitted to the remote database (data collection private network 240 and/or the master database 250) associated with the unique code via the network interface service 241, or a combination thereof. In an alternate embodiment, the machine may be operated, but readings of the user's blood pressure will not be transmitted to the remote database or stored on the user identification device.

The data collection private network 240 has one or more data bases 250, 251, 252 disposed on one or more servers. Those skilled in the art understand that all data could be held in one database on one server. However, those skilled in the art also understand the advantages of partitioning databases among one or more servers in order to spread the load of traffic over several servers and thereby provide overall faster system response. For example, a second database 251 may hold data by country or Partner. A further database 252 may be for administrative purposes and hold reports and statistics. The network 240 has processing modules 255 that import and export information and send data to Partners and end users. Other file resources include, for example, advertisements, firmware, images, etc that may be accessed by Partners for use at the deployed locations.

The network 240 provides different network interface services ("NIS") for handling communications between the network 240 and locations, end users, trusted sources and Partners. For example, MS 243 is a web-based blood pressure tracker. It interfaces a user to the user's data in the user's account so that the user may track recorded blood pressure readings from any personal computer or network enabled device 260. NIS 224 interfaces with health information entities to provide access to the databases 250-253. NIS 246 interfaces Partners and their employees for administrative management of web-based reporting. The respective NISs 241-246 receive data from the various sources 210, 260, 261 and 262, parse the data into predetermined fields, and distribute the data to other parts of the network as required.

The data in the database 250 are accessible to the user via a personal computer, mobile phone, or other network enabled devices 260. One or more trusted sources, such as the user's physician, pharmacist, or a health agency 261 may have limited or unrestricted access to one or more user records in the database 250 via information associating the unique code with the user. Examples of such health agencies include and are not limited to insurance companies, electronic medical record keepers, patient user identification device monitoring entities, and web-based personal health records companies such as Microsoft HealthVault and Google's personal health records web site. Further examples include the National Institutes of Health, medical data mining agencies or any other health agency that is conducting a clinical study. The data may also be given to the user on a local display 218. The display may show the most recent reading along with a history of a selected number of the most recent readings. As a further option, the machine 210 may be connected to a printer (not shown) and the current test results and the most recent results displayed on the screen can be printed for the user. Alternatively, a user may preselect that the results not be displayed on the screen and have such results output only on the printer.

The user identification device 201 bears an identification code either in a machine (scanner) readable form such as a one-dimensional or two-dimensional barcode stored in an electronic memory and presented on a display screen of the user identification device when the user activates the code display function, or as a printed bar code on an exterior surface of the user identification device 201. The identification code may also be stored on a card in a magnetic strip format. The identification may also be in a human readable form so that the user may input the unique code via a keypad access mechanism. As described above, the first three characters in the code may be used to identify the issuer of the code. The user identification device 201 does not bear the name of the user and the issuer does not record the name or identity of the user. The user identification device 201 may be given to the user free of charge if the user identification device is in the form of a card or smart card, or for a nominal fee. Similarly, if the user identification device is intended as a smart phone or other electronic communication device, then the software app may be downloaded to the device free of charge or for a nominal charge. Only the authorized user of the user identification device 201 may associate the data stored in database 250 with the identity of the user, or may authorize someone else to make such an association. No other party has access to the identity of the user unless the user permits such access.

The user does not have to take any further action to record data to the database 250. Each time the user inserts, displays, or otherwise provides the user identification device 201 to the kiosk 210, the readings stored in the user identification device are uploaded to the database 250 via the network 219 or 280. The data from user identification device 201 may be stored in a file of the database, e.g. a user account, identified by the code AAP-XXX-ZZZ which may appear on the face of the user identification device in human readable form, machine readable form, or a combination thereof. It may be stored internally in the user identification device 201 in digital electronic form. If biometric data is used to identify authorized users, then the biometric identifier information is associated with the unique access code at one of the remote databases described herein, e.g. at the data collection private network 240 and/or the master database 250 associated with the unique code.

In order to gain access to the stored data, the user may log into the web based network interface service 243, which is a front end user interface to the database 250. Upon login, a conventional security program may ask for the user's PIN, unique access code, request birth data information, ask a security question, or any combination thereof. If this is the first time the user is logging in, the system may ask the user to establish a PIN and/or record answers to one or more security questions, such as "In what city were you born." The user is free to share his or her unique access code, or PIN or security information with other trusted sources, such as a physician, a pharmacy, or a clinical agency 261. Other exemplary software interfaces and platforms for accessing a user's health data include, but are not limited to web based delivery to desktops, tablets, and phones; smart phone native applications; short message service (SMS) text messaging interface; interactive voice response system; application programming interfaces (APIs) to exchange data with other health data marts, such as Microsoft HealthVault; and PharmaSmart plug-ins which integrate with leading Pharmacy Electronic Medical Record (PEMR) and Medication Therapy Management (MTM) systems.

The user identification device 201 does not carry the identity of the user, nor does any data exchanged between machine 201 and the remote databases 250-252, or between the user identification device and the remote databases, contain user identity information. The invention has additional embodiments usable in non-medical contexts for any application that gathers, stores, and recalls a limited number of data values on a replenishable basis as described herein.

One such application is transit systems, wherein an embodiment records a charge to a user's account deductible at each stage of a journey on a transit system. At each stage of the journey, the embodiment notes the time and location of the user's entry for travel, and deducts one or more credit increments as appropriate for the stage on which the user is embarking. The user may afterwards obtain from the user identification device a record of travel for business or evidentiary reasons.

Another application is a library or other lending system, wherein the embodiment charges a user identification device with lending credit increments deductible by the user when borrowing a book, film, music score, or other item of rental or lease of goods or equipment. Different items borrowed may result in different numbers of credit increments being deducted. The embodiment stores the time and date of lending or rental and the time and date of return of the item on the user identification device.

In its basic embodiment, a network uses an apparatus and a process, developed initially for the PharmaSmart Model PS-2000C blood pressure machine and similar machines made by others. The PS-2000C is equipped to use blood pressure user identification devices or user identification devices to store blood pressure readings for the end user. It is likely that millions of these blood pressure user identification devices or user identification devices will eventually be in circulation in North America and in other parts of the world. The embodiment provides the option for Locations to: 1) generate additional revenues by charging the end user an annual fee for use of the user identification device, and 2) provide end user with at least one annual blood pressure consultation.

Figure 2:
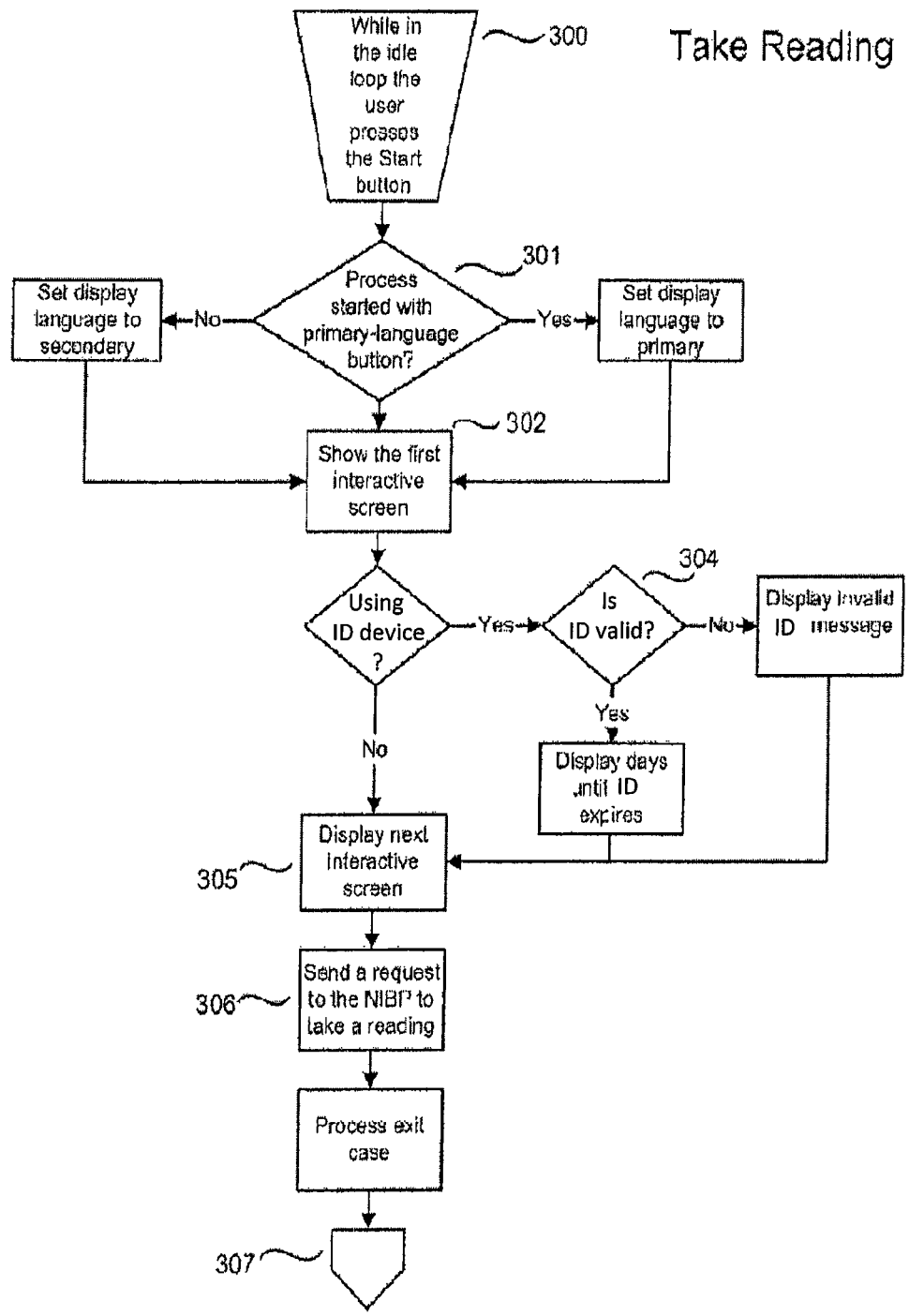
FIGS. 2, 3, 4 are flow charts demonstrating algorithms for using an exemplary user identification device.
Figure 3:
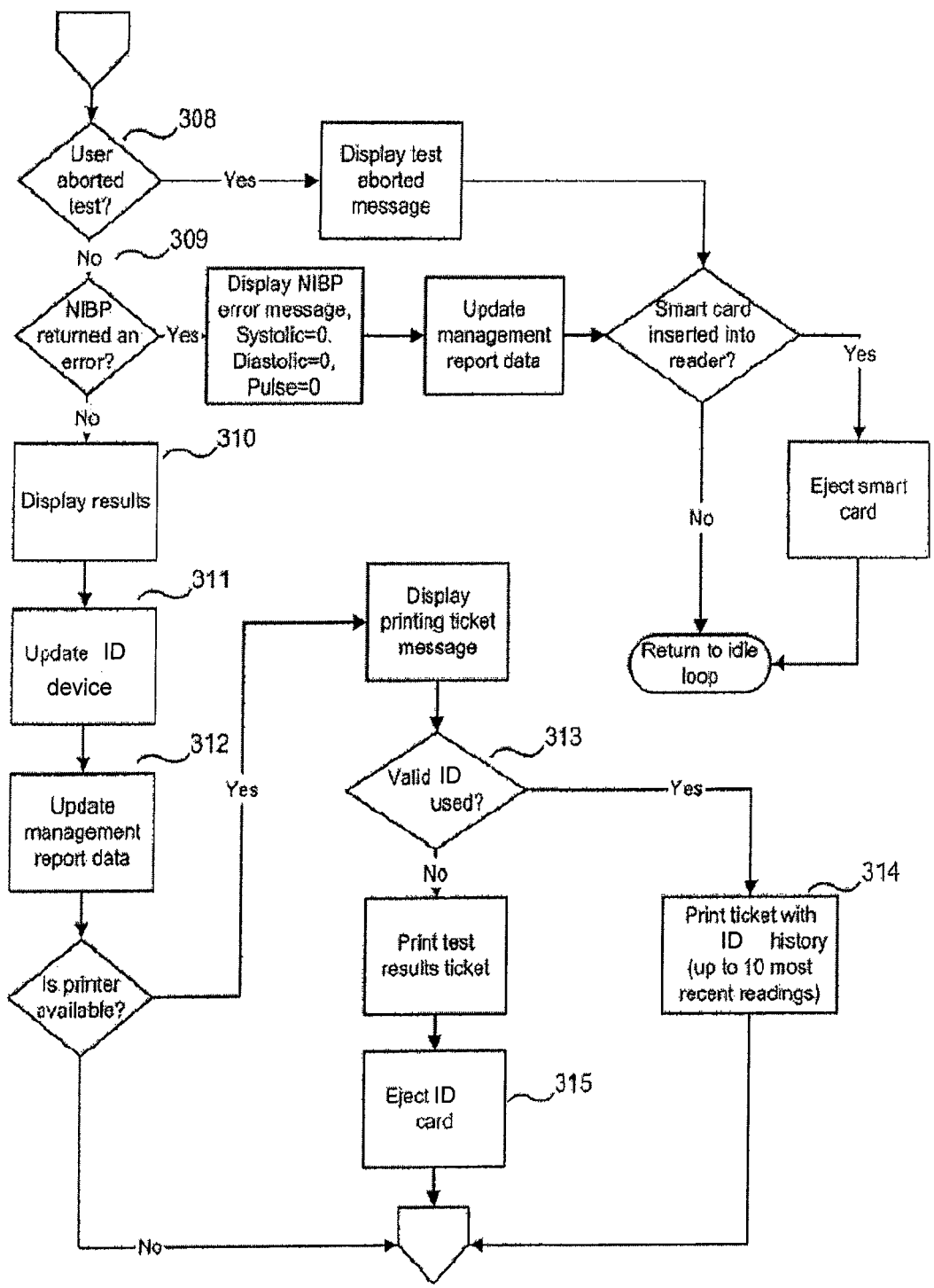
Figure 4:
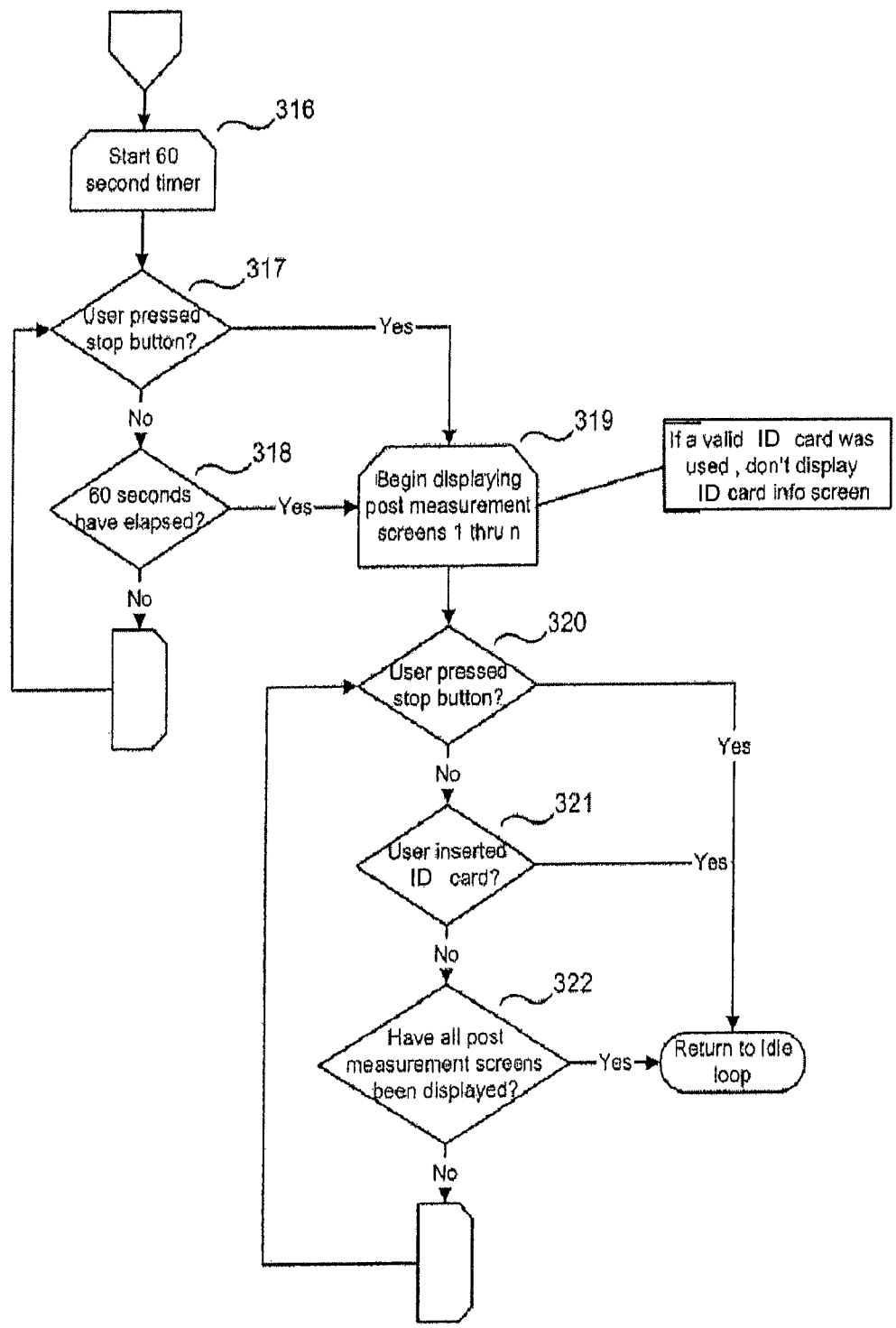

Turning to FIGS. 2-4 there is a basic flow chart of steps for operation of the kiosk 210 using a user identification device 201. In step 300, the user has entered, inserted or presented the user identification device at an user identification device reader or scanner and then presses the Start button on the machine 210. The program checks for the primary language of the user 310 and then shows the use a first interactive screen 302 on the display 218. Step 304 checks to see if the user identification device is a valid user identification device. If it is, the program displays a number of days remaining before expiration, advances to step 305 and displays the next interactive screen. At step 306, the user requests a reading and the machine 210 inflates the cuff and gradually reduces the pressure in the cuff to take a non-invasive blood pressure (NIBP) reading in step 307. Unless the user aborts the test 308 or there is machine error 309, the reading is displayed on the machine's display 310, stored on the user identification device 311, and sent 312 to the master database 250 in the form of a management report. If a printer is available the user identification device is validated a second time 313 and a ticket is printed with a set of the most recent readings, for example, the last ten readings 314. If the user identification device is in the form of a smart card embodiment inserted into the machine, then the smart card may be ejected from the machine 315. Next, the machine enters a wait state routine (steps 316-322) to see if the user wants to take another reading. Upon completion of the wait state routine with no further user input, the machine returns to its idle loop 300.

In an alternate embodiment of the invention, the user identification device may be a card without memory and/or microprocessor, but is simply a card with a printed machine readable code thereon, such as a customer loyalty card. The user identification device may also comprise a hand held electronic communication device having a simplified software app that calls up a stored bar code for presentation on a display of a hand held electronic device. The bar code in either embodiment may be a one dimensional bar code, or a two dimensional bar code such as a QR code. The user may have a PIN or unique access code associated with the user identification device, but the user's name appears nowhere on the user identification device or in any data transmitted between the user identification device and the kiosk, or between the kiosk and the database. If the user identification device is lost or stolen, the user's data on the network is secure. Even if one obtains the data associated with the user identification device, or the user identification device itself, without authorization from the user, the identity of the user identification device holder remains unknown to that person.

The kiosks 210 may use an alternative, optional reauthorization or replenishment feature (herein after "recharge"). As used herein, the terms "reauthorization" and "recharge" have the same meaning. The term "recharge" is not used in the sense of a rechargeable battery that can receive and hold electrical energy. Instead, the term "recharge" is intended to indicate a date after which the user identification device will no longer work for its intended purposes. With this feature, the first time the end user uses the user identification device in the machine; it electronically "stamps" a recharge (i.e. expiration) date into a smart card embodiment of the user identification device. Alternatively, an expiration date may be recorded on the user identification device, or stored at the database in association with the user's account, or a combination of these options may be implemented. The recharge date is a fixed or variable date, but preferably is one (1) year from the date of first use in the machine. This means the end user has a full year of use of the user identification device before it will require a recharge. If the user identification device is not recharged by the recharge date, it will no longer work in the machine.

Many retailers want branded user identification devices or identifiable smart phone software apps that drive the user back to the same retailer. For example, a regional or national pharmacy chain would like the user to always visit a location of the retail pharmacy in order to use the user identification device. This system also enables exclusivity by user identification device issuer. For example, the blood pressure machines can be configured to accept only user identification devices or user identification devices with codes bearing the first three characters "AAP". Therefore, user identification devices or user identification devices issued by another retailer or organization could not be utilized in the blood pressure machines located in "All American Pharmacies". In addition, the retailer may set limits on the number of times the user identification device may be used. By requiring the user return to the retailer to recharge or reauthorize the user identification device, the system would induce the user to return to one of the establishments in the retailer's chain in order to reauthorize the user identification device for additional uses. The retailer may reauthorize the user identification device free of charge or for a nominal fee. In either case, the user identification device is reauthorized with a new set of credits for its use.

At any time, the Location may purchase recharge credits directly from the manufacturer of the ABP machine. These credits may be loaded onto a unique "Recharge user identification device", and shipped directly to the Location. Upon the end user's request, the Location personnel can access a Recharge account to recharge the end user's user identification device for an additional year. In order to do this the Location personnel may have a Recharge authorized user identification device and the end user identification device in hand. They then simply register the Recharge user identification device into the ABP machine and follow the instructions provided on the machine's display. Once completed, an updated recharge date is electronically "stamped" onto the end user identification device providing another time period, for example, a full year, of use of the user identification device. Each time the Location personnel recharges an end user identification device, the Recharge authorized account is debited one (1) recharge credit. Once all of the recharge credits are used, the Location personnel may order additional Recharge credits from the ABP machine manufacturer. The kiosk manufacturer may charge Partners a fee for each recharge credit they order, and the Partner can charge the end user an annual fee for allowing the user to access its kiosks.

Figure 5:
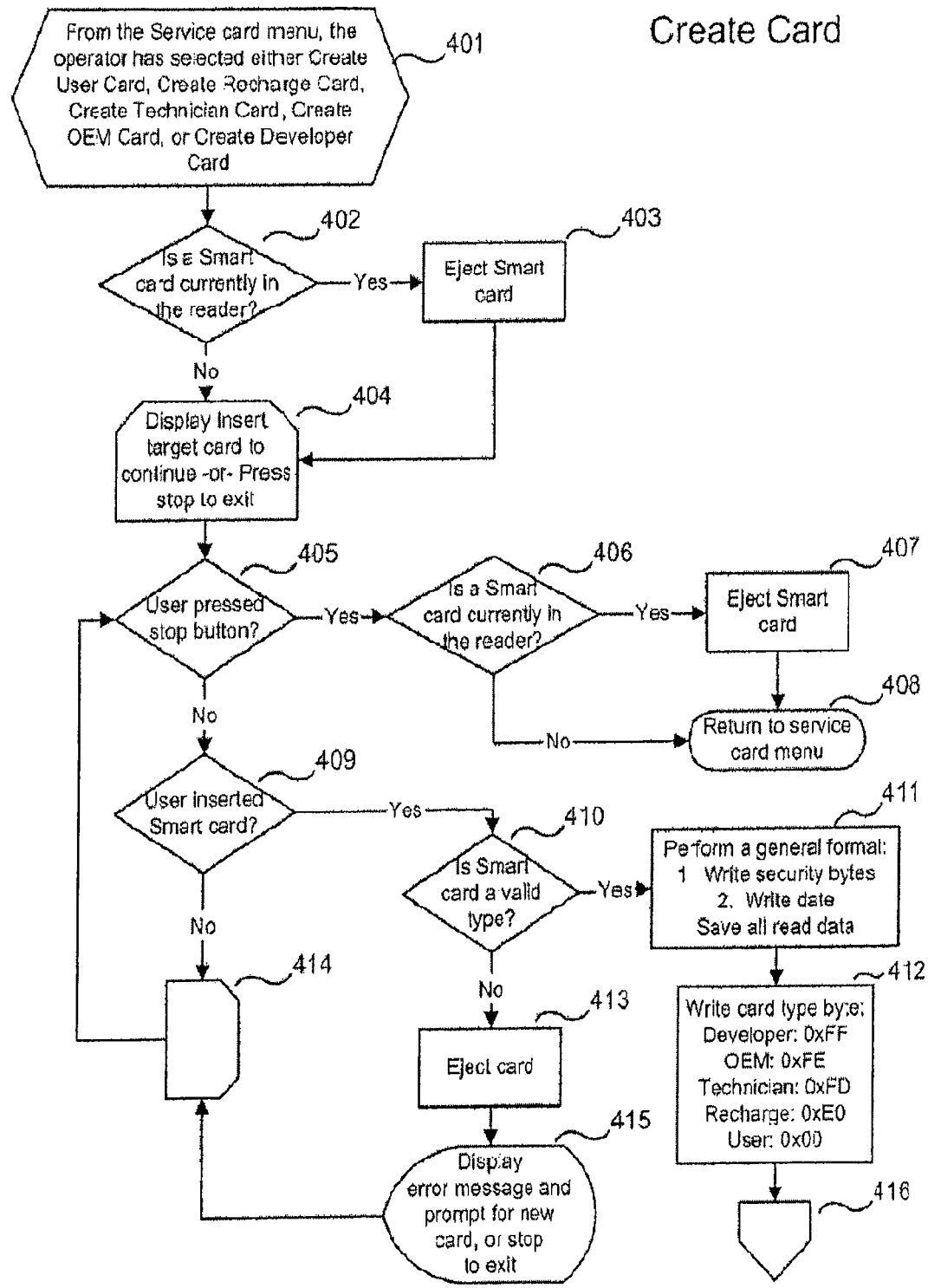
FIGS. 5, 6 are a flow chart of steps for creating an exemplary user identification device.
Figure 6:
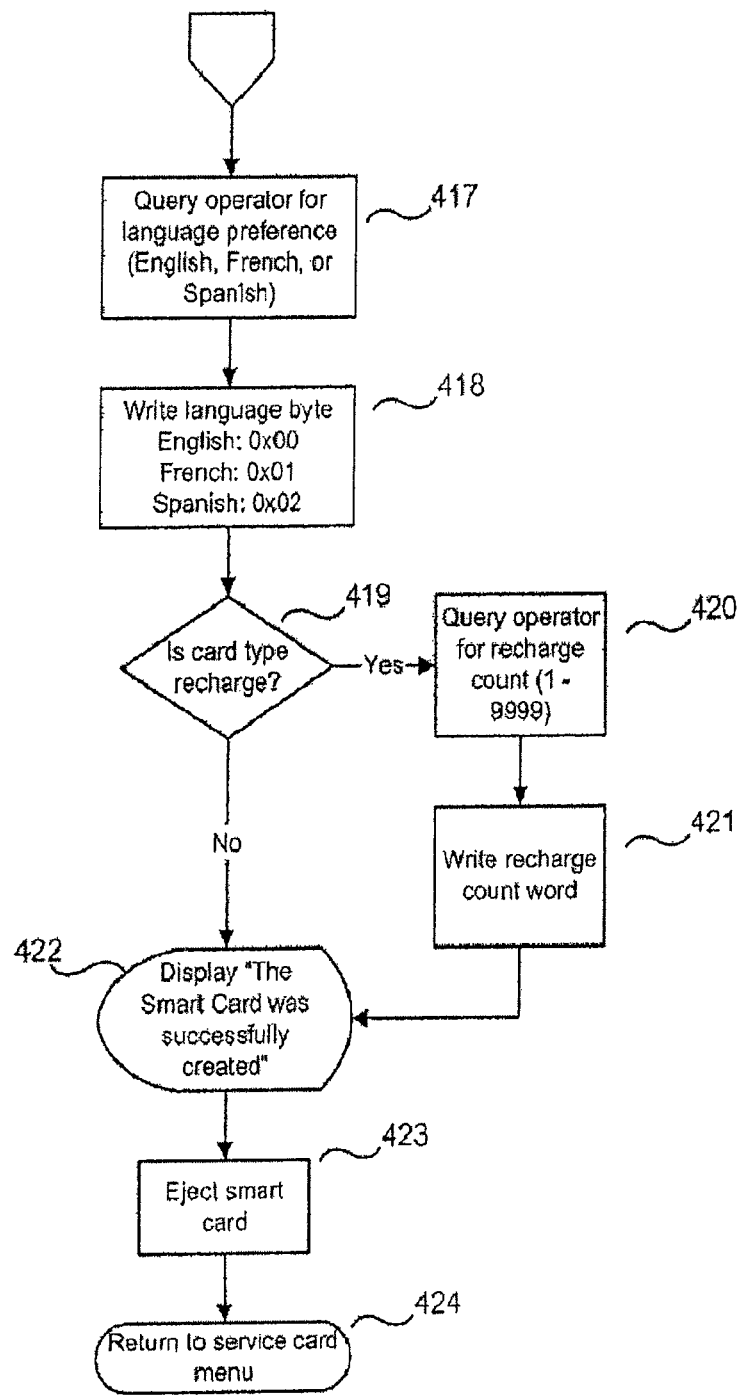

With reference to FIG. 4, there is illustrated a method of operating the kiosk 210 for creating a smart card embodiment of a user identification device. User identification devices and member identification information are created in the kiosk 210 following steps 401-424 as shown in FIGS. 5, 6. The operator at a Partner location has a Recharge card. When the operator places the Recharge card in a reader, the menu appears with one or more selections including a selection to "Create OEM Card." The operator inserts 404 a blank OEM smart card into the reader. Unless the user-operator stops the operation 405, the smart card is evaluated to see if it is a valid type, i.e., one that is recognized and acceptable by the system. If so, the system performs a number of operations 411,412 on the smart card to format the card, add security bytes, and record the OEM and other administrative data. If it is not a valid smart card 410, it is ejected 413. Assuming the smart card is valid, the operator may then set the language preference 417 for the user identification device. If the smart card is a Recharge Card 419, the operator is asked for its number of counts or recharges and is ejected 423.

In the alternative, the retail location may add credits associated with the user identification device free of charge. As a further alternative, the retail location may authorize unlimited use of the user identification device. In that case, the memory on the user identification device is configured to store data on a first in, first out basis and the data on the user identification device is always the most recent data acquired by using the user identification device.

Figure 7:
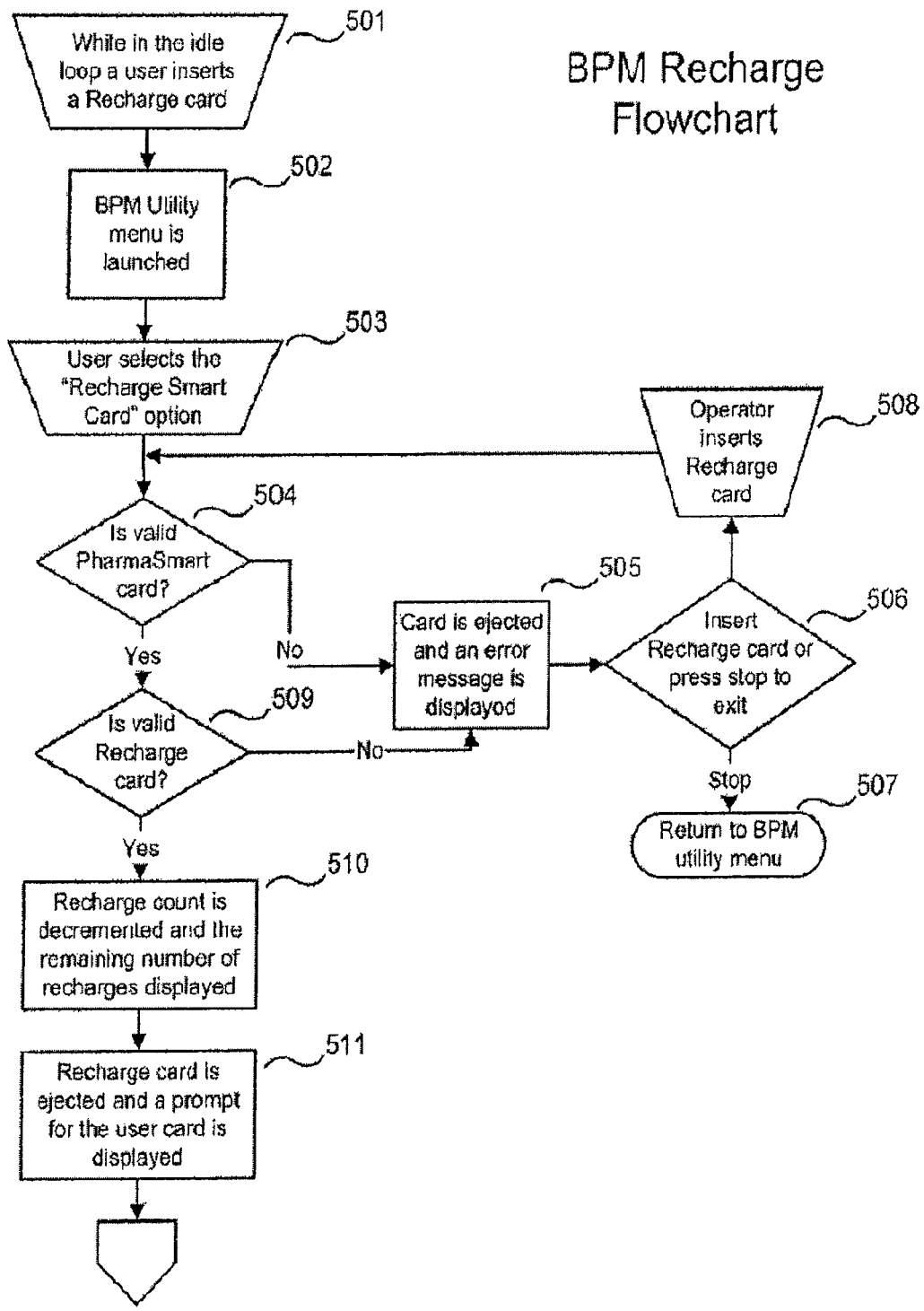
FIGS. 7, 8 are a flow chart of steps for replenishing an exemplary user identification device account.
Figure 8:
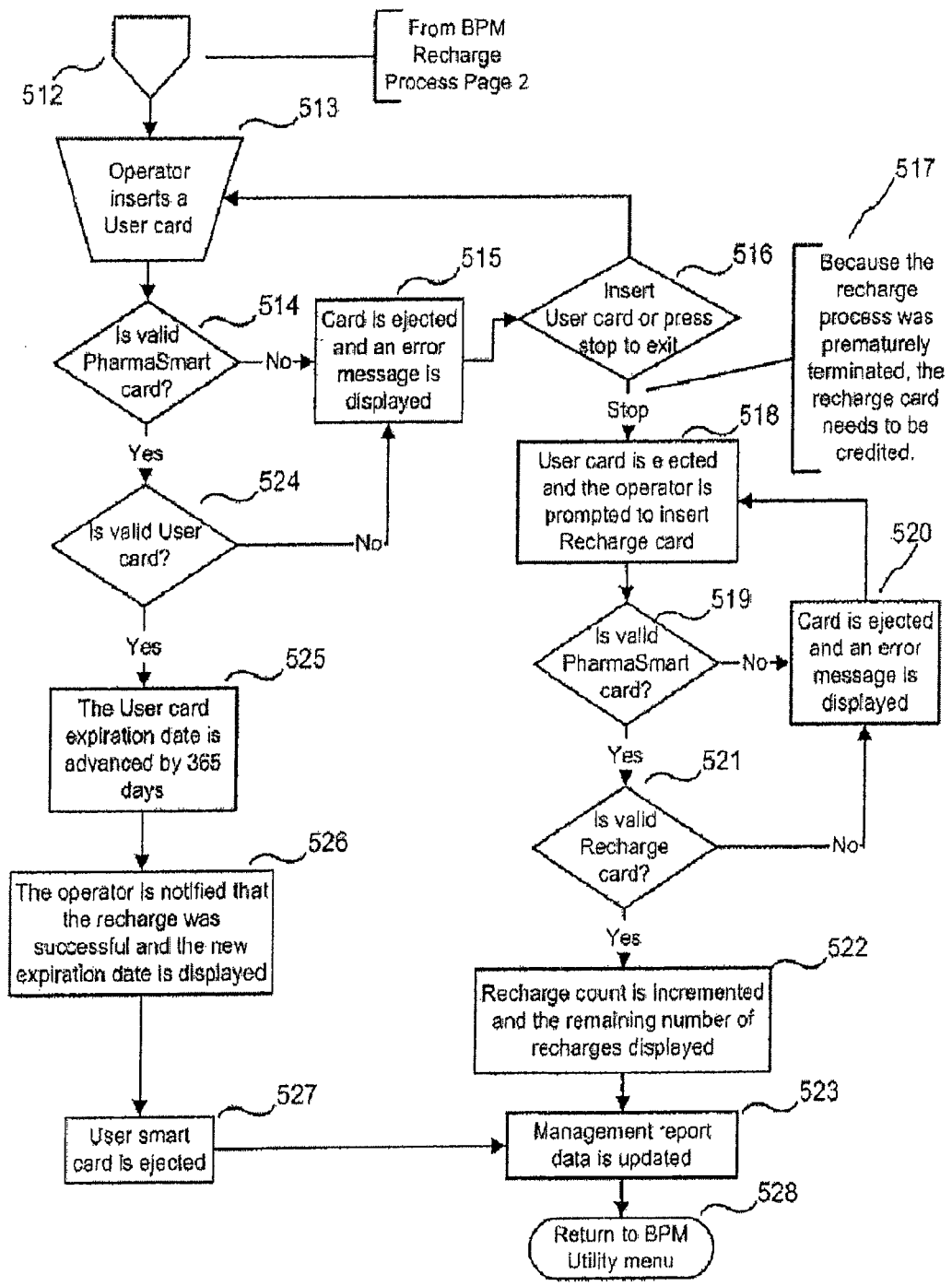
Figure 9:
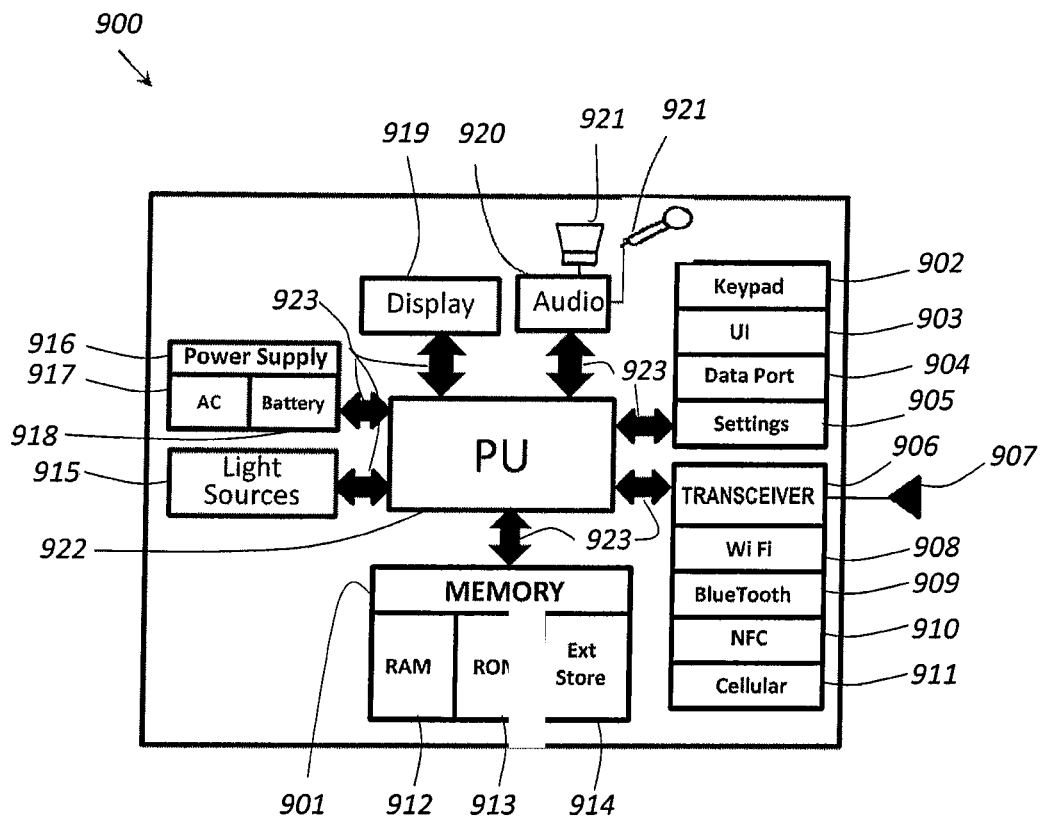
FIG. 9 is a schematic diagram of an exemplary user identification device embodiment.

FIGS. 7-9 show a combined flow chart presenting specific software design and operational details of the smart card embodiment recharge process as performed using a single-port user identification device reader. There are three overall parts of the recharge process: 1) updating the Recharge card, 2) updating the smart card, and 3) restoring the Recharge card to an earlier state when a user smart card update has not been completed. Steps 501-528 are steps of the updating of a Recharge card. The operator inserts the Recharge card in the card reader 501. The system presents the ABP machine utility menu to the operator 502. The operator selects 503 the "Recharge smart card" option from the menu. The system reads the Recharge card contents. If the card is not a valid PharmaSmart card of any type, the system displays 506 a message to that effect and prompts the user to use a PharmaSmart Recharge card and ejects 505 the invalid user identification device. If the user identification device is a valid PharmaSmart Recharge card 509, the system decrements 510 the card's Recharge count, and displays the number of recharges remaining on the card, ejects the Recharge card, and prompts the operator to insert the user smart card. Once the Recharge card is decremented one credit, the user Smart card updating process begins. The operator inserts 513 the User's smart card. If the card is not a valid PharmaSmart card of any type, the system displays 515 a message to that effect and prompts the user to use a PharmaSmart user smart card. If the card is a valid PharmaSmart card, the system advances 525 the card's Expiration Date by 365 days, or if the Expiration Date has passed, sets a new Expiration Date 365 days from the User smart card's update. The system notifies 526 the operator of the successful update and displays the total number of days until the user's smart card will require another recharge. The system ejects 527 the user smart card. The system updates 523 its management report data, and returns to display 501 the ABP machine's utility menu. During the user smart card update, the operator may decide that the recharge process cannot be completed. If the process is not completed, the Recharge card and the user smart card are left in states that are mutually inconsistent. The Recharge card indicates that a recharge has been done, while the user smart card has not been recharged. Consequently, the inconsistency should be corrected. The Recharge card should be incremented one Recharge Credit. See step 517.

In a general embodiment providing for storage and analysis of non-invasive physiological test data and other medical monitoring information, the user identification device may record values from automated equipment for reading blood glucose level, blood cholesterol level, or other testable medical parameter values. The range of testable medical parameter values expands constantly as new technologies enable rapid, reliable, low-powered monitoring techniques to be packaged and made available to an end user. The user identification device records the non-invasive physiological test data that the user took over the course of a year. The user can use the user identification device to access this entire history at any Location, and print out the most recent 10 entries or all of them. The average of the printed entries is given with the printout. The date of each reading may also be recorded on the user identification device and printed alongside each entry, allowing the user or a physician to identify trends in the data. Additionally, at the user's request, the data from the user identification device can be loaded into the computer system of a pharmacy or doctor's office, allowing health care workers quick access to the user's non-invasive physiological test data.

At a Location, the user can print out the entire history of non-invasive physiological test data stored on the user identification device. Additionally, at a pharmacy or physician's office this data can be submitted for a consultation on the patient's condition. When the user identification device is recharged, an option is given to allow the user to submit his data to a pharmacy for a consultation. Tests now performed in a laboratory, such as blood enzyme levels for such critical markers as creatine phosphokinase (CPK), will eventually be capable of being performed properly and inexpensively in a manner similar to that now used for blood pressure monitoring. Furthermore, evaluations requiring significant analysis and processing of data, such as the classification of cardiac arrhythmias requiring medical attention, may become capable of being performed in a consumer setting as well.

Finally, numerous drugs, such as the COX-2 inhibitors, can produce varied deleterious effects on small subsets of their users. The monitoring of blood markers for adverse or allergic reactions to such drugs presents another field of application for the present invention. To record the values captured in one embodiment, the embodiment substitutes different value sets and ranges for different types of reading and different sensitivity requirements. For example, readings of blood glucose levels when fasting range from the 60-100 range (excellent) to above 180 (poor), but after a meal the range rises so that the 110-140 range represents an excellent level, while above 220 represents a poor level of blood glucose (source of values: University of Massachusetts Medical School Web page concerning self-monitoring of blood glucose levels using the lancet). Ranges for different classes of monitored values are represented in the embodiments of the invention using range classifications, biasing of values, elimination of non-significant digits of precision, and other techniques well-known in the art for compressing data values for storage in limited memory space.

In a secure embodiment, the invention incorporates conventional anti tampering hardware and software components in the user identification device and the Recharge card to prevent an end user, a Location employee, or a thief from using a conventional standalone card reader to alter the contents of the user identification device or the Recharge card. In the secure embodiment, the invention applies encryption to the contents of the card, rendering the contents of the card unreadable by any process except the decryption of the encrypted values. The Location employee (for the Recharge card) or the end user (for the user identification device) reads and updates the user identification device's contents by furnishing the decryption key for the card or device. The specific encryption techniques used are well-known in the art and so are not described here.

Any attempt to read the smart card's contents using a conventional standalone card reader triggers the execution of software which breaks open one or more fuses on the card, rendering the card useless. While such measures do not prevent fraudulent misuse of the card, they make such misuse considerably more difficult. The operation, contents, encryption, and decryptions of the embodiments of the invention's Recharge card are the same for all classes of data to be collected.

With reference to FIG. 9, there is illustrated an exemplary block diagram of a hand held electronic communication device 900, such as a smart phone, compatible with the system and network described herein for managing access to a controlled resource. The block diagram illustrates a portion of internal electronic components of the communication device that may be used for implementing the invention described herein. Those skilled in the art will recognize that a smart phone embodiment of a communication device will include further modules and components in addition to those illustrated in FIG. 9. For example, a smart phone may include a SIM card connected to the processor 922, as well as analog-digital converters, audio coder/decoders, digital signal processors, chips or chip sets for a radio baseband processing section between the processor 922 and the antenna 907, an image sensor for a camera component, a vibrator motor for non-audio operation, various transmission and receiver circuits, such as amplifiers, filters, oscillators, and logic circuits, etc. which are not shown in FIG. 9 for ease of illustration and description relevant to embodiments of the invention disclosed herein.

Such a communication device may include a processing system 922, as illustrated in FIG. 9, disposed within an interior of the device housing. A keypad of the communication device may be operable via a keypad module 902 for allowing the entry of data, to prompt an output of data, to navigate menus presented on a display of the communication device managed by a user interface module 903, and to execute commands. User inputs may be requested via prompts presented on a display of the device controlled via display module 919 connected to processor 922. The keypad may include mechanical switches, or a touch screen interface with virtual buttons may also be utilized.

The electronic components of the hand held communication device 900 can be disposed on, for example, a printed circuit board situated within a housing. The processor 922 may be in the form of a microprocessor, a microcontroller, or an application specific integrated circuit ("ASIC"), and may include a mixed signal processor ("MSP"), a field programmable gate array ("FPGA"), or a combination thereof, and is electrically connected to the various electronic modules included on, or connected to, the printed circuit board. The processor 922 is electrically connected to the various modules via communication lines 923. The display module 919, which may include a display processor and display buffer, is electrically connected to the processor 922 over the communication line 923 for receiving and displaying output data, and for displaying user interface input options under control of processor 922. The structure of the user interface, such as menu options, is stored in user interface module 903 and is accessible by processor 922 for presenting menu options to a user of the communication device 900. An audio module 920 includes a speaker and microphone 921, 924, respectively, for outputting and receiving audio data stored or received by the device 900. Audio outputs can include, for example, voice communications, reminders, and alarms, or may include audio data to be replayed in conjunction with display data presented via the display module 919. A volume of the audio output is controlled by the processor 922, and the volume setting can be stored in settings module 905 together with other default device settings, as determined by the processor or as adjusted by the user. Although not shown, the communication device 900 may include a vibration motor for outputting a reminder in the form of a vibration or to otherwise notify the user when the audio is turned off.

The brightness of the display may be controlled by the processor 922 via a light source control module 915. Default brightness settings of all light sources, as well as settings adjusted by the user, are stored in a settings module 905, which is accessible and adjustable by the processor 922. A memory module 901, comprising volatile random access memory ("RAM") 912, a non-volatile memory 913, which may comprise read only memory ("ROM") or flash memory, and a circuit 914 for connecting to an external portable memory device via a data port, is electrically connected to the processor 922 over a communication line 923. External memory devices may include flash memory devices housed in thumb drives, portable hard disk drives, data cards, or any other form of electronic storage devices. The on-board memory can include various embedded applications executed by the processor for operation of the communication device 900. On board memory can also be used to store a history of a user's blood pressure measurements dates and times associated therewith and images of one or two dimensional bar codes and other identification information for presentation on the display. Using the wireless transmission capability of the communication device or a data port 904, such measurement data can be transferred via wired or wireless transmission to connected computers, the remote database described herein, or other processing devices.

Transceiver 906 circuits for wireless digital data transmission and reception via one or more internal digital antennas 907 is electrically connected to the processor 922 over communication line 923. The wireless transceiver circuits may be in the form of integrated circuit chips, chipsets, programmable functions operable via processor 922, or a combination thereof. Each of the wireless transceiver circuits may be compatible with a different wireless transmission standard. For example, a wireless transceiver circuit 908 may be compatible with the Wireless Local Area Network IEEE 802.11 standard known as WiFi. Transceiver circuit 908 is configured to detect a WiFi access point in proximity to the communication device 900 and to transmit and receive data from such a detected WiFi access point. A wireless transceiver circuit 909 may be compatible with the Bluetooth protocol and is configured to detect and process data transmitted from a Bluetooth "beacon" in proximity to the communication device 900. A wireless transceiver circuit 910 may be compatible with the near field communication ("NFC") standard and is configured to establish radio communication with, for example, an NFC compliant kiosk 210 at a retail merchant in proximity to the communication device 900. A wireless transceiver circuit 911 may comprise a circuit for cellular communication with cellular networks and is configured to detect and link to available cellular communication towers. The electronic communication device 900 may include programming that allows the device to communicate with a kiosk via the Bluetooth, NFC, or cellular interface including transmitting health record information. The kiosk can also verify an authorized user by automatically wirelessly requesting the user's unique identification code from the electronic communication device.

A power supply module 916 is electrically connected to all modules in the communication device housing and to the processor 922 to supply electric power thereto. The power supply module 916 may comprise a rechargeable battery pack 918 or an AC power supply 917 may be activated when the communication device 900 is connected to a source of AC power. The power supply module 916 is also electrically connected to processor 922 over the communication line 923 such that processor 922 can monitor a power level remaining in a battery pack power mode of the power supply module 916.

In addition to connecting external storage for use by the communication device 900, the data port 904 can be used to accept a suitable connector attached to a connecting lead, thereby allowing the communication device 900 to be connected by wire to an external device such as kiosk 210 or a personal computer. Data port 904 can be any port that allows for transmission of data such as, example, a serial, USB, or a parallel port.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

What is claimed is:

1. A system comprising:
  a database configured to be coupled to a public wide area network resident on an electronic reader via a network service interface where said database has an identifier for each user that does not disclose said user's identity;
  one or more non-invasive physiological test machines configured to be coupled to the public wide area network, the physiological test machines registered at the database for performing one or more non-invasive physiological tests for authorized users;
  a plurality of electronic readers each associated with at least one of the physiological test machines for controlling use thereof and for reading machine readable code storable on a communications device presented to the electronic reader, the machine readable code having associated therewith a number of remaining authorized uses, an authorized time period, and an identification code associated with an authorized user where said identifier coordinates with the user and an identifier in the central database; and history code comprising the history of the user non-invasive measurements;

each non-invasive physiological test machine having a test results display for showing non-invasive physiological test results acquired by the non-invasive physiological test machines from the authorized user;

each non-invasive physiological test machine having a transmitter coupled to the public wide area network;

each transmitter configured to send data representative of the non-invasive physiological test results associated with the identification code to the database via the network service interface; and the database for receiving the data from the transmitter and for storing records of the non-invasive physiological test results according to the identification code, wherein the machine readable code, the identification code, and the data representative of the non-invasive physiological test results do not carry information representative of the identity of the authorized user.

2. The system of claim 1, wherein the machine readable code is stored in a hand held communication device, and the device comprises a display for presenting the machine readable code to the electronic reader.

3. The system of claim 1, wherein the machine readable code is stored in a hand held communication device, and the device comprises a transmitter for transmitting the machine readable code to the electronic reader.

4. The system of claim 1, wherein the electronic readers communicate the identification code to the database for verifying the authorized user, the number of remaining authorized uses, and the authorized time period.

5. The system of claim 2, wherein the database comprises a transmitter for sending the machine readable code to the communication device via the network service interface.

6. The system of claim 2, wherein the database sends the machine readable code to the communication device over the public wide area network prior to each time the authorized user requests said non-invasive physiological test.

7. The system of claim 3, wherein the machine readable code is transmitted to the electronic reader by the device upon the device receiving a communication from the electronic reader requesting verification.

8. The system of claim 7, wherein the device comprises a near field communication (NFC) circuit for wirelessly transmitting the machine readable code to the electronic reader.

9. The system of claim 2, wherein the database comprises a transmitter for sending the physiological test results to the device.

10. The system of claim 2, wherein the database comprises a transmitter for transmitting the identification code to the device of an authorized user in a human readable form and in a machine readable form.

11. The system of claim 1, further comprising one or more computers connected to the public wide area network with authority to access data in the database associated with the identification code.

12. The system of claim 9, wherein the device comprises a memory for storing the physiological test results.

13. The system of claim 12, wherein the memory includes flash memory, optical memory, magneto-optical memory, a miniature hard disks drive, or a combination thereof.

14. The system of claim 2, wherein the device comprises a memory for storing the authorized number of uses for the authorized time period.

15. The system of claim 1, further comprising means for authorizing further uses and for extending the authorized time period.

16. The system of claim 1, wherein the test machines are each configured to conduct a blood pressure test.

17. The system of claim 1, wherein the display is a monitor or a printer.

18. A system comprising:
electronic code readers, transmitters connected to a network, one or more controlled resources, a network service interface, and a database;

wherein the code readers are configured to read a machine readable code storable on a communications device comprising a unique code, and a history of non-invasive physiological tests, the unique code associated with data corresponding to an authorized number of uses for an authorized period of use for an authorized user;

the code readers disposed at locations for controlling access to one or more controlled resources by a user who has presented the machine readable code to the code reader;

the code readers responsive to said machine readable code for determining the authorized number of uses and the authorized period of use corresponding to the unique code and for permitting the user to the controlled resources so long as the unique code has at least one authorized use remaining within the authorized period of use and for denying permission to use the controlled resources if there are no authorized uses remaining or the authorized period of use is expired;

a display communicatively coupled to the code reader for showing the number of remaining authorized uses and the expiration date of the authorized period of use corresponding to the unique code;

each transmitter coupled to at least one of the controlled resources for sending data over the network representative of the location of the code reader, the use of the controlled resource and the time of use of the controlled resource;

the database connected to the network via a network service interface for receiving and storing the data from the transmitters in accordance with the unique code, wherein the machine readable code, the unique code, the data corresponding to an authorized number of uses for an authorized period of use for an authorized user, and the data from the transmitters do not carry data representative of the identity of the authorized user.

19. A system comprising:
a database configured to be coupled to a publicly accessible network via a network service interface;

a plurality of account files stored in the database, each account file having associated therewith a unique code and an authorized number of uses for an authorized time period for an authorized user;

a plurality of electronic readers for reading machine readable code storable on a communications device, the machine readable code including the unique code associated with the account file of the authorized user, and for controlling use of non-invasive physiological test machines;

one or more non-invasive physiological test machines for performing one or more non-invasive physiological tests on the authorized user where such non-invasive test machines are in a publicly available kiosk;

each non-invasive physiological test machine having a display for showing non-invasive physiological test results acquired by the non-invasive physiological test machines;

each non-invasive physiological test machine having a transmitter coupled to the publicly accessible network;

each transmitter configured to send data representative of the non-invasive physiological test results over the publicly accessible network to the database via the network service interface; and the database for receiving transmissions from the non-invasive physiological test machine transmitter for storing records of the non-invasive physiological test results according to the unique code.

20. The system of claim 19, wherein the electronic readers include one of a laser scanner for reading one dimensional machine readable code, a laser scanner for reading two dimensional machine readable code, a laser scanner for reading a QR code, a retinal scanner, a finger print scanner, facial recognition software, or a combination thereof.

* * * * *